US00PP09560P

United States Patent [19]

Trees

[11] Patent Number: Plant 9,560

[45] Date of Patent: May 21, 1996

[54] GERANIUM PLANT NAMED 'BFP-817 LIGHT SALMON'

[75] Inventor: Scott C. Trees, Arroyo Grande, Calif.

[73] Assignee: Geo. J. Ball, Inc., West Chicago, Ill.

[21] Appl. No.: 432,264

[22] Filed: May 1, 1995

[51] Int. Cl.[6] ..... A01H 5/00

[52] U.S. Cl. ..... Plt./87.12

[58] Field of Search ..... Plt./87.12

*Primary Examiner*—James R. Feyrer

*Attorney, Agent, or Firm*—Burns, Doane, Swecker & Mathis

[57] ABSTRACT

A new and distinct *Pelargonium×hortorum* cultivar named 'BFP-817 Light Salmon' is provided. This new Zonal Geranium cultivar was the result of a controlled breeding program wherein a plant designated 1919-39 (non-patented in the United States) was pollinated by a plant designated 3928-1 (non-patented in the United States). The new cultivar forms attractive semi-double pastel salmon florets in a freely-flowering display. Attractive dark green foliage with slight zonation is well retained during shipment. The growth habit is medium to vigorous self-branching and does not require the use of a growth regulator.

1 Drawing Sheet

SUMMARY OF THE INVENTION

The present invention comprises a new and distinct Geranium cultivar, botanically known as *Pelargonium×hortorum* Bailey, and hereinafter is referred to by the cultivar name 'BFP-817 Light Salmon'.

The new cultivar is a product of a planned breeding program which had the objective of the creation of a new Geranium cultivar that exhibits uniform flowers, dark green foliage, a medium self-branching growth habit that requires no growth regulator, a propensity for rapid rooting, and a stable foliage coloration during shipment.

The breeding program that resulted in the production of the new cultivar of the present invention was carried out in a controlled environment during 1992 at Arroyo Grande, Calif., U.S.A. The female parent (i.e., seed parent) was a plant designated 1919-39 (non-patented in the United States) which exhibited light pink semi-double florets and medium green foliage. The male parent (i.e., pollen parent) was a plant designated 3928-1 (non-patented in the United States) which exhibited single light pink florets and dark green foliage. The parentage of the new 'BFP-817 Light Salmon' cultivar can be summarized as follows:

1919-39×3928-1.

'BFP-817 Light Salmon' was discovered and selected during 1992 as a highly distinctive flowering plant from among the progeny of the stated cross at Arroyo Grande, Calif., U.S.A. This plant was initially designated BFP-817.

It was found that the new cultivar of the present invention:

(a) exhibits attractive semi-double pastel salmon florets in a freely-flowering display, (b) forms attractive dark green foliage with slight zonation, and (c) exhibits a medium to vigorous self-branching growth habit in the absence of a growth regulator.

When plant material of the 'BFP-817 Light Salmon' cultivar is subjected to standard random amplified polymorphic DNA marker analysis (RAPD) using polymerase chain reaction (PCR) and a known set of DNA primers, it is found to exhibit a distinctive fingerprint map which is on file at the Ball FloraPlant Division of Geo. J. Ball, Inc. at Arroyo Grande, Calif., U.S.A.

The first act of asexual reproduction of the 'BFP-817 Light Salmon' cultivar was accomplished when vegetative cuttings were taken from the initial selection in a controlled environment at Arroyo Grande, Calif., U.S.A., by a technician working under the direction and supervision of the originator of the new cultivar. Horticultural examination of plants resulting from such asexual propagation during 1993 has demonstrated that the combination of characteristics as herein described for the 'BFP-817 Light Salmon' cultivar is firmly fixed and is retained through successive generations of such asexual reproduction.

The new 'BFP-817 Light Salmon' cultivar has not been observed under all possible environmental conditions. Accordingly, the described phenotype may vary somewhat with variations in the environment, such as temperature, light intensity, and day length.

Of the many commercial cultivars, the 'Eclipse Light Salmon' cultivar (U.S. Plant Pat. No. 7,926) is considered to be the most similar to the new 'BFP-817 Light Salmon' cultivar. When the new cultivar of the present invention is compared to the 'Eclipse Light Salmon' cultivar, it is found that the 'BFP-817 Light Salmon' cultivar exhibits slightly larger florets (e.g., approximately 4.2 to 5.0 cm. in diameter vs. approximately 4.3 to 4.6 cm.), shorter pedicels (e.g., approximately 2.9 to 3.7 cm. vs. approximately 3.6 to 4.3 cm.), and larger leaves (e.g., 10.2 to 11.2 cm.×approximately 9.0×9.5 cm. vs. approximately 9.5 to 10.7 cm.×approximately 8.5 to 9.0 cm.).

The new cultivar of the present invention is being marketed by Geo. J. Ball, Inc. under the SHOWCASE trademark.

BRIEF DESCRIPTION OF THE PHOTOGRAPHS

The accompanying photograph of FIG. 1 shows a typical plant of the new 'BFP-817 Light Salmon' cultivar with colors generally being as nearly true as it is reasonably possible to make the same in color illustrations of this character. Fully-opened umbels and contrasting dark green foliage are illustrated. The plant was being grown in a greenhouse at West Chicago, Ill., U.S.A.

DETAILED DESCRIPTION

Figure 1:
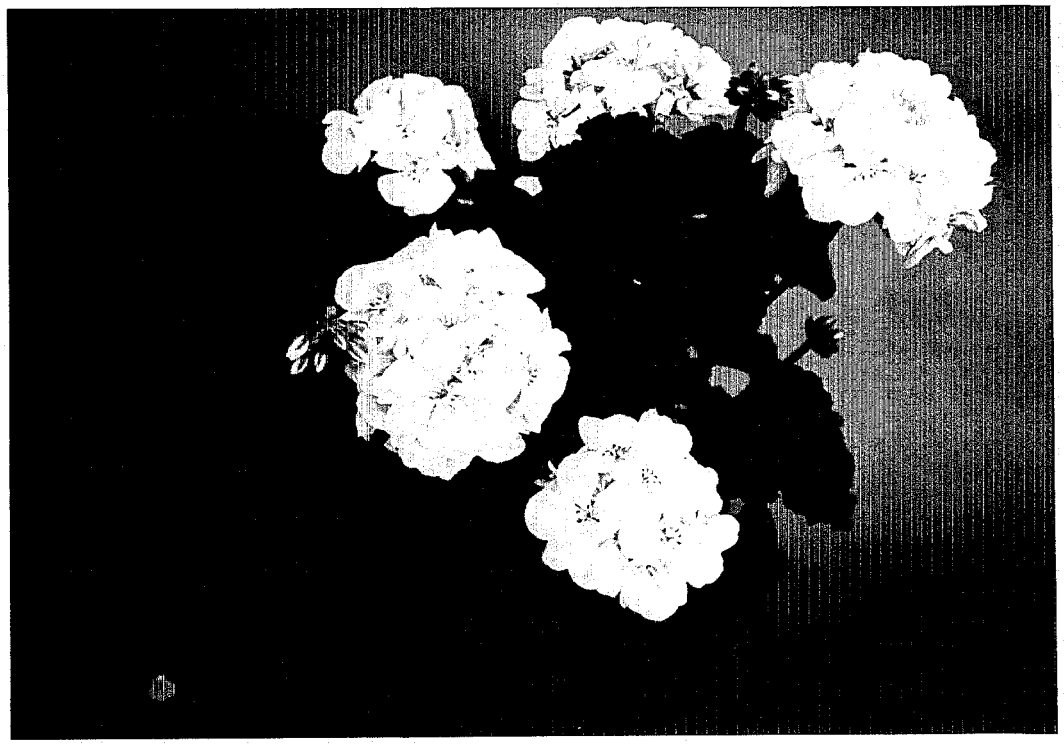

The following observations, measurements and comparisons describe plants grown in Ball FloraPlant's greenhouses at West Chicago, Ill., U.S.A. under greenhouse conditions which approximate those generally used in commercial practice. In the following description, color references are made to the R.H.S. Color Chart of The Royal Horticultural Society, London, England. The color values were determined on Jan. 3, 1995, under natural light conditions of 2,000 footcandles.

Classification:

*Botanical.*—*Pelargonium×hortorum* Bailey, cv. 'BFP-817 Light Salmon'.

*Commercial.*—Zonal Geranium.

Inflorescence

A. Umbel:

*Average diameter.*—Approximately 10.0 to 12.0 cm. compared to approximately 9.5 to 11.5 cm. for the 'Eclipse Light Salmon' cultivar.

*Average depth.*—Approximately 6.9 to 7.1 cm. compared to approximately 5.0 to 7.3 cm. for the 'Eclipse Light Salmon' cultivar.

*Peduncle length.*—Approximately 13.0 to 18.5 cm. compared to approximately 14.5 to 17.5 cm. for the 'Eclipse Light Salmon' cultivar.

*Pedicel length.*—Approximately 2.9 to 3.7 cm. compared to approximately 3.6 to 4.3 cm. for the 'Eclipse Light Salmon' cultivar.

*Number of umbels plant.*—When grown in a 10 cm. pot at 9 weeks after the sticking of a rooted cutting, there commonly are 3 to 4 umbels per plant. This same number of umbels per plant commonly is exhibited by the 'Eclipse Light Salmon' cultivar.

*Number of florets umbel.*—When grown in a 10 cm. pot at 9 weeks after the sticking of a rooted cutting, there commonly are approximately 30 to 39 florets per umbel. This compares to approximately 27 to 40 florets per umbel for the 'Eclipse Light Salmon' cultivar.

B. Corolla:

*Average diameter.*—Approximately 4.2 to 5.0 cm. compared to approximately 4.3 to 4.6 cm. for the 'Eclipse Light Salmon' cultivar.

*Form.*—Both the 'BFP-817 Light Salmon' cultivar and the 'Eclipse Light Salmon' cultivar are semi-double with petaloids and each floret commonly possesses approximately 6 to 7 petals.

*Number of petaloids.*—The 'BFP-817 Light Salmon' cultivar commonly forms approximately 1 to 2 petaloids per floret and the 'Eclipse Light Salmon' cultivar commonly forms approximately 1 to 3 petaloids per floret.

*Color.*—General tonality from a distance of three meters: Light salmon. Adaxial: Red Group 49C. This compares to Red Group 49D for the 'Eclipse Light Salmon' cultivar. Abaxial: Red Group 49D. This compares to Red Group 48C with veins of Red Group 56D for the 'Eclipse Light Salmon' cultivar.

C. Bud:

*Shape.*—Oval-rounded.

*Color.*—Adaxial: Red Group 49C compared to Red Group 49D for the 'Eclipse Light Salmon' cultivar. Abaxial: Red Group 49D compared to Red Group 48C for the 'Eclipse Light Salmon' cultivar.

D. Reproductive organs:

*Androecium.*—The anthers are commonly approximately 2 mm. in length. The pollen color for both the 'BFP-817 Light Salmon' cultivar and the 'Eclipse Light Salmon' cultivar is Orange-Red Group 33A. The filaments commonly are approximately 4 to 6 mm. in length.

*Gynoecium.*—The pistil length commonly is approximately 8 to 9 mm. There is a single stigma which commonly has a length of approximately 4 mm. which commonly branches into 5 parts, and, the style length commonly is approximately 5 mm.

*Fertility.*—Usually does not produce fruits in the absence of mechanical fertilization.

E. Spring flowering response period: Approximately 6 to 7 weeks from rooted cuttings under standard greenhouse conditions.

F. Outdoor flower production: Freely flowering under outdoor growing conditions with substantially continuous blooming.

G. Durability: Ships well.

Plant

A. Foliage: Dark green with slight zonation.

*Form.*—Reniform, with cordate base.

*Margin.*—Crenate.

*Color.*—Adaxial: Yellow-Green 147A for both the 'BFP-817 Light Salmon' cultivar and the 'Eclipse Light Salmon' cultivar. Abaxial: Yellow-Green Group 147B. This compares to Green Group 137C for the 'Eclipse Light Salmon' cultivar.

*Size.*—Approximately 10.2 to 11.2 cm. at the widest point and approximately 9.0 to 9.5 cm. at the narrowest point. This compares to approximately 9.5 to 10.7 cm. at the widest point and approximately 8.5 to 9.0 cm. at the narrowest point for the 'Eclipse Light Salmon' cultivar. A medium self-branching growth habit is exhibited in the absence of the use of a growth regulator.

B. General appearance and form:

*Internode length.*—Commonly varies from approximately 2.0 to 3.0 cm. This compares to approximately 1.5 to 3.0 cm. for the 'Eclipse Light Salmon' cultivar.

*Branching pattern.*—Freely basal branching. No pinching is required to obtain self-branching. A medium self-branching growth habit is exhibited in the absence of the use of a growth regulator.

*Height.*—Approximately 27 to 34 cm. above a 10 cm. pot at 9 weeks under standard greenhouse conditions. This compares to approximately 27 to 32 cm. for the 'Eclipse Light Salmon' cultivar.

I claim:

1. A new and distinct Geranium plant named 'BFP-817 Light Salmon', substantially as herein shown and described, which:

(a) exhibits attractive semi-double pastel salmon florets in a freely-flowering display, (b) forms attractive dark green foliage with slight zonation, and (c) exhibits a medium to vigorous self-branching growth habit in the absence of a growth regulator.

* * * * *